US012678609B2

(12) United States Patent
Sanikommu

(10) Patent No.: US 12,678,609 B2
(45) Date of Patent: Jul. 14, 2026

(54) SPLIT SEPTUM NEEDLE FREE CONNECTOR AND POST NEEDLE FREE CONNECTOR WITH SLEEVE SEPTUM FUSE CONCEPT

(71) Applicant: CareFusion 303, Inc, San Diego, CA (US)

(72) Inventor: Narsi Reddy Sanikommu, Prakasam district (IN)

(73) Assignee: CAREFUSION 303, INC., San Diego, CA (US)

( * ) Notice: Subject to any disclaimer, the term of this patent is extended or adjusted under 35 U.S.C. 154(b) by 783 days.

(21) Appl. No.: 18/098,630

(22) Filed: Jan. 18, 2023

(65) Prior Publication Data

US 2024/0238576 A1     Jul. 18, 2024

(51) Int. Cl.
*A61M 39/10* (2006.01)
*A61M 39/22* (2006.01)
(Continued)

(52) U.S. Cl.
CPC ........ *A61M 39/10* (2013.01); *A61M 39/1011* (2013.01); *A61M 39/22* (2013.01);
(Continued)

(58) Field of Classification Search
CPC .... A61M 2039/1066; A61M 2039/267; A61M 2039/262; A61M 39/26; A61M 2039/0054; A61M 39/165
(Continued)

(56) References Cited

U.S. PATENT DOCUMENTS 5,492,147 A * 2/1996 Challender ............. F16L 37/28
604/905
5,713,856 A 2/1998 Eggers et al.
(Continued)

FOREIGN PATENT DOCUMENTS

EP 0681493 B1 6/2000
EP 1678070 A2 7/2006
(Continued)

OTHER PUBLICATIONS

Bangert, Bill, "Shorter times to blood transfusion associated with decreased death risk in trauma patients", Medical Xpress, Apr. 14, 2016, https://medicalxpress.com/news/2016-04-shorter-blood-transfusion-decreased-death.html.
(Continued)

*Primary Examiner* — Jason E Flick
*Assistant Examiner* — Isabella S North
(74) *Attorney, Agent, or Firm* — MASCHOFF BRENNAN

(57) ABSTRACT
Fluid connectors assemblies that provide neutral fluid displacement are disclosed. A fluid connector assembly may include first member and a second member. A deformable sleeve is located on a post of the second member. A septum is located on an opening of the first member. The first member and the second member each include an opening. The sleeve can seal off the opening of the post from fluid entry. However, when the post of the second member is inserted into the first member, a septum of the first member displaces a sleeve of the second member, causing the sleeve to uncover the opening. Further, the septum seals each of the first member and the second member and the displaced sleeve forms a fluid path through the first and second member, with the sleeve regulating fluid flow.

18 Claims, 5 Drawing Sheets

(51) Int. Cl.
*A61M 5/14* (2006.01)
*A61M 39/26* (2006.01)

(52) U.S. Cl.
CPC ....... *A61M 5/14* (2013.01); *A61M 2039/1072*
(2013.01); *A61M 39/26* (2013.01); *A61M*
*2039/267* (2013.01)

(58) Field of Classification Search
USPC ..................................... 604/256; 137/614.05
See application file for complete search history.

(56) References Cited

U.S. PATENT DOCUMENTS

| | | | |
|---|---|---|---|
| 6,146,362 A * | 11/2000 | Turnbull | A61M 39/045 |
| | | | 604/905 |
| 6,874,522 B2 | 4/2005 | Anderson et al. | |
| 7,004,934 B2 | 2/2006 | Vaillancourt | |
| 7,040,598 B2 | 5/2006 | Raybuck | |
| 7,153,296 B2 | 12/2006 | Mitchell | |
| 7,350,764 B2 | 4/2008 | Raybuck | |
| 7,396,051 B2 | 7/2008 | Baldwin et al. | |
| 7,763,013 B2 | 7/2010 | Baldwin et al. | |
| 7,766,394 B2 | 8/2010 | Sage et al. | |
| 7,794,675 B2 | 9/2010 | Lynn | |
| 7,803,139 B2 | 9/2010 | Fangrow, Jr. | |
| 7,803,140 B2 | 9/2010 | Fangrow, Jr. | |
| 7,815,614 B2 | 10/2010 | Fangrow, Jr. | |
| 7,918,243 B2 | 4/2011 | Diodati et al. | |
| 7,998,134 B2 | 8/2011 | Fangrow et al. | |
| 8,123,738 B2 | 2/2012 | Vaillancourt | |
| 8,142,418 B2 | 3/2012 | Mcmichael et al. | |
| 8,211,069 B2 | 7/2012 | Fangrow, Jr. | |
| 8,262,628 B2 | 9/2012 | Fangrow, Jr. | |
| 8,361,408 B2 | 1/2013 | Lynn | |
| 8,480,968 B2 | 7/2013 | Lynn | |
| 8,777,908 B2 | 7/2014 | Fangrow, Jr. | |
| 8,777,909 B2 | 7/2014 | Fangrow, Jr. | |
| 8,795,256 B1 | 8/2014 | Smith | |
| 8,888,758 B2 | 11/2014 | Mansour | |
| 8,899,267 B2 | 12/2014 | Diodati et al. | |
| 8,910,919 B2 | 12/2014 | Bonnal et al. | |
| 8,974,425 B2 | 3/2015 | Tachizaki et al. | |
| 8,974,437 B2 | 3/2015 | Williams et al. | |
| 9,114,242 B2 | 8/2015 | Fangrow et al. | |
| 9,126,028 B2 | 9/2015 | Fangrow et al. | |
| 9,126,029 B2 | 9/2015 | Fangrow et al. | |
| 9,192,753 B2 | 11/2015 | Lopez et al. | |
| 9,234,616 B2 | 1/2016 | Carrez et al. | |
| 9,358,379 B2 | 6/2016 | Fangrow, Jr. | |
| 9,433,769 B2 | 9/2016 | Bayly | |
| 9,468,749 B2 | 10/2016 | Mansour et al. | |
| 9,492,649 B2 | 11/2016 | Carrez et al. | |
| 9,636,492 B2 | 5/2017 | Fangrow, Jr. | |
| 9,724,504 B2 | 8/2017 | Fangrow, Jr. et al. | |
| 9,724,505 B2 | 8/2017 | Williams et al. | |
| 9,861,805 B2 | 1/2018 | Dennis et al. | |
| 9,933,094 B2 | 4/2018 | Fangrow | |
| 9,974,939 B2 | 5/2018 | Fangrow, Jr. | |
| 9,974,940 B2 | 5/2018 | Fangrow, Jr. | |
| 10,029,086 B2 | 7/2018 | Nowak et al. | |
| 10,156,306 B2 | 12/2018 | Fangrow | |
| 10,173,045 B2 | 1/2019 | Mansour | |
| 10,179,203 B1 | 1/2019 | Huslage et al. | |
| 10,315,025 B2 | 6/2019 | Phillips et al. | |
| 10,398,887 B2 | 9/2019 | Fangrow, Jr. et al. | |
| 10,426,701 B2 | 10/2019 | Py | |
| 10,441,507 B2 | 10/2019 | Sanders | |
| 10,518,078 B2 | 12/2019 | Stjernberg Bejhed et al. | |
| 10,569,073 B2 | 2/2020 | Hallisey et al. | |
| 10,625,068 B2 | 4/2020 | Leuthardt et al. | |
| 10,655,768 B2 | 5/2020 | Jones et al. | |
| 10,697,570 B2 | 6/2020 | Fangrow | |
| 10,744,315 B2 | 8/2020 | Sanders | |
| 10,842,982 B2 | 11/2020 | Fangrow, Jr. | |
| 10,857,346 B2 | 12/2020 | Dennis et al. | |

| | | | |
|---|---|---|---|
| 10,864,362 B2 | 12/2020 | Jones et al. | |
| 10,881,847 B2 | 1/2021 | Lynn | |
| 11,168,818 B2 | 11/2021 | Fangrow | |
| 11,207,514 B2 | 12/2021 | Kakinoki | |
| 11,235,135 B2 | 2/2022 | Tsai | |
| 11,273,297 B2 | 3/2022 | Kakinoki | |
| 11,484,471 B2 | 11/2022 | Sanders | |
| 11,491,084 B2 | 11/2022 | Ueda et al. | |
| 2004/0215158 A1 | 10/2004 | Anderson | |
| 2005/0090805 A1 | 4/2005 | Shaw et al. | |
| 2006/0129109 A1 | 6/2006 | Shaw et al. | |
| 2007/0088292 A1 | 4/2007 | Fangrow, Jr. | |
| 2007/0088293 A1 | 4/2007 | Fangrow, Jr. | |
| 2007/0088294 A1 | 4/2007 | Fangrow, Jr. | |
| 2007/0225635 A1 | 9/2007 | Lynn | |
| 2008/0039803 A1 | 2/2008 | Lynn | |
| 2008/0076960 A1 * | 3/2008 | Marseille | A61M 25/0662 |
| | | | 604/165.01 |
| 2011/0106046 A1 | 5/2011 | Hiranuma | |
| 2014/0114292 A1 * | 4/2014 | Tachizaki | F16L 37/30 |
| | | | 604/533 |
| 2014/0249487 A1 | 9/2014 | Lynn | |
| 2014/0330254 A1 | 11/2014 | Rosenberger et al. | |
| 2016/0000363 A1 | 1/2016 | Jones et al. | |
| 2017/0202741 A1 * | 7/2017 | Py | A61M 39/18 |
| 2018/0200147 A1 | 7/2018 | Sanders | |
| 2019/0184152 A1 | 6/2019 | Kakinoki | |
| 2019/0282797 A1 | 9/2019 | Tsai | |
| 2020/0113784 A1 | 4/2020 | Lopez et al. | |
| 2020/0179672 A1 | 6/2020 | Kakinoki | |
| 2020/0215319 A1 | 7/2020 | Fangrow, Jr. et al. | |
| 2020/0284385 A1 | 9/2020 | Fangrow | |
| 2020/0323734 A1 | 10/2020 | Ueda et al. | |
| 2020/0338331 A1 | 10/2020 | Sanders | |
| 2021/0069484 A1 | 3/2021 | Tsai | |
| 2021/0077803 A1 | 3/2021 | Lynn | |
| 2021/0252267 A1 | 8/2021 | Fangrow, Jr. | |
| 2021/0388926 A1 | 12/2021 | Martin et al. | |
| 2021/0393938 A1 | 12/2021 | Lynn et al. | |
| 2022/0260189 A1 | 8/2022 | Deuse | |
| 2022/0282814 A1 | 9/2022 | Fangrow | |

FOREIGN PATENT DOCUMENTS

| | | | |
|---|---|---|---|
| EP | 1517723 B1 | 1/2007 | |
| EP | 1622675 B1 | 8/2009 | |
| EP | 2144634 A1 | 1/2010 | |
| EP | 2298407 A1 | 3/2011 | |
| EP | 2694132 A1 | 2/2014 | |
| EP | 2562456 B1 | 6/2014 | |
| EP | 2782633 A1 | 10/2014 | |
| EP | 1842002 B1 | 4/2015 | |
| EP | 2736582 B1 | 5/2015 | |
| EP | 2089094 B1 | 1/2016 | |
| EP | 2219721 B1 | 12/2017 | |
| EP | 2753396 B1 | 12/2017 | |
| EP | 2736584 B1 | 4/2018 | |
| EP | 3305361 A1 | 4/2018 | |
| EP | 2271398 B1 | 11/2018 | |
| EP | 2480281 B1 | 11/2018 | |
| EP | 2790750 B1 | 11/2018 | |
| EP | 2331191 B1 | 3/2019 | |
| EP | 3079756 B1 | 3/2019 | |
| EP | 2121114 B1 | 5/2019 | |
| EP | 2719419 B1 | 5/2019 | |
| EP | 2956204 B1 | 8/2019 | |
| EP | 3421077 B1 | 8/2019 | |
| EP | 3530313 A1 | 8/2019 | |
| EP | 3538201 A1 | 9/2019 | |
| EP | 3570807 A1 | 11/2019 | |
| EP | 3570809 A1 | 11/2019 | |
| EP | 2536463 B1 | 4/2020 | |
| EP | 3381505 B1 | 5/2020 | |
| EP | 3538201 B1 | 5/2020 | |
| EP | 1904152 B1 | 12/2020 | |
| EP | 2150307 B1 | 12/2020 | |
| EP | 3313490 B1 | 1/2021 | |
| EP | 3760275 A1 | 1/2021 | |
| EP | 3851155 A1 | 7/2021 | |

(56)                     References Cited

FOREIGN PATENT DOCUMENTS

| EP | 3517164 B1 | 9/2021 |
| EP | 3954355 A1 | 2/2022 |
| EP | 3960229 A1 | 3/2022 |
| EP | 3973044 A1 | 3/2022 |
| EP | 3305361 B1 | 5/2022 |
| EP | 3134052 B1 | 8/2022 |
| EP | 3530313 B1 | 8/2022 |
| WO | WO-2021099437 A1 | 5/2021 |
| WO | WO-2021180675 A1 | 9/2021 |
| WO | WO-2021252197 A1 | 12/2021 |
| WO | WO-2022042956 A1 | 3/2022 |
| WO | WO-2022149339 A1 | 7/2022 |
| WO | WO-2022207560 A1 | 10/2022 |

OTHER PUBLICATIONS

Icumedical, "ChemoClave™ Needlefree Close System Transfer Device (CSTD)", date unknown, https://www.icumed.com/products/oncology/closed-system-transfer-devices/chemoclave.

Icumedical, "ChemoLock™ Needlefree Closed System Transfer Device (CSTD)", date unknown, https://www.icumed.com/products/oncology/closed-system-transfer-devices/chemolock.

Ivteam, "Force-activated separation IV connectors", 2022, Retrieved from the internet https://www.ivteam.com/intravenous-literature/force-activated-separation-iv-connectors/ [Last retrieved Jan. 13, 2023].

Lineus Medical, SafeBreak Product Features and Benefits Brochure, May 2021, mkg 0058 5/21 Rev. 02.

PRZen, "Lineus Medical Goes International, Signs ONEY for Distribution in Korea", PRZen Online Press Release Distribution, PrZen/33448014, MKG-0130 Rev 00, Retrieved from the internet https://przen.com/pr/lineus-medical-goes-international-signs-oney-for-distribution-in-korea-przen-33448014 [Last retrieved Jan. 13, 2023].

Rickard, et al., "Securing All intraVenous devices Effectively in hospitalised patients—the SAVE trial: study protocol for a multicentre randomised controlled trial", BMJ Open, Sep. 23, 2015;5(9):e008689, doi: 10.1136/bmjopen-2015-008689. PMID: 26399574; PMCID: PMC4593168.

Tada Group AB, LinkedIn Post "ReLink granted patent in Japan", LinkedIn, Mar. 2022, retrieved from the internet https://se.linkedin.com/company/tadamedical?trk=public_post_reshare_feed-actor-image&original_referer= [Last retrieved Mar. 2022].

Tribology, "Coefficient of friction, Rolling resistance and Aerodynamics", date unknown, https://www.tribology-abc.com/abc/cof.htm.

International Search Report and Written Opinion for Application No. PCT/US2024/011807, dated Apr. 25, 2024, 15 pages.

* cited by examiner

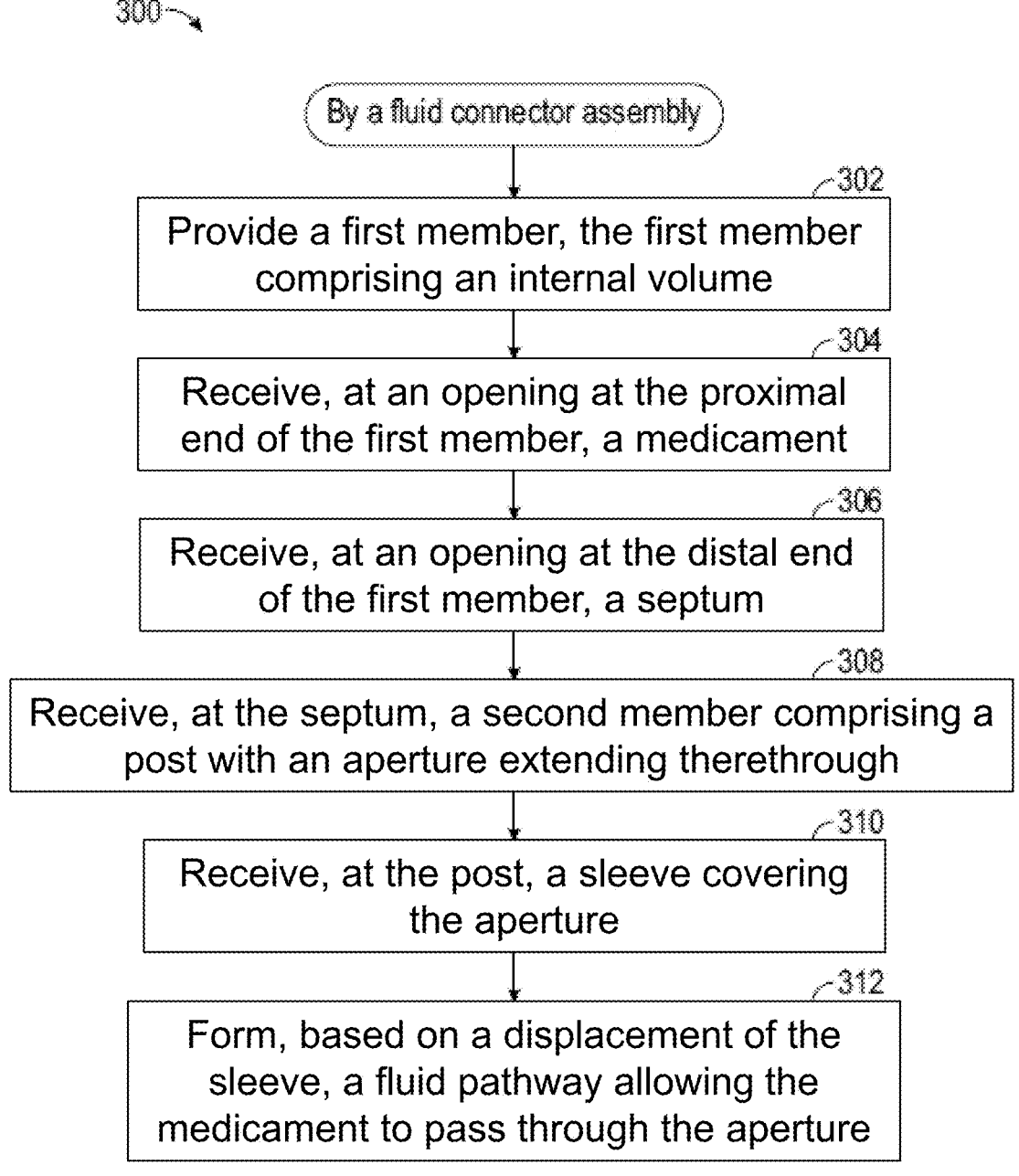

300

By a fluid connector assembly

302
Provide a first member, the first member comprising an internal volume

304
Receive, at an opening at the proximal end of the first member, a medicament 306
Receive, at an opening at the distal end of the first member, a septum 308
Receive, at the septum, a second member comprising a post with an aperture extending therethrough 310
Receive, at the post, a sleeve covering the aperture 312
Form, based on a displacement of the sleeve, a fluid pathway allowing the medicament to pass through the aperture

FIG. 5

SPLIT SEPTUM NEEDLE FREE CONNECTOR AND POST NEEDLE FREE CONNECTOR WITH SLEEVE SEPTUM FUSE CONCEPT

TECHNICAL FIELD

The present disclosure relates generally to medical fluid connectors and, more particularly, to neutral displacement needle-free connectors that reduce the occurrence of dislodgment of an intravenous (IV) catheter that is connected to a patient.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Often, tubing or catheters are coupled or secured to each other to allow fluid communication between various portions of tubing or catheters.

Needle-free connectors, including neutral displacement needle-free connectors, offer a solution for providing medical fluid to patients. In an exemplary embodiment, a needle-free connector assembly promotes fluid transmission between a medical fluid supply and a catheter line. The medical fluid supply and the catheter line are secured to respective luers. To transmit fluid, the luer connected to the medical supply overlaps a central post of the luer connected to the catheter line.

In some applications, such tubing or catheters may become dislodged due to improper securement and/or when the needle-free connector is subject to forces greater than what the coupling is designed to withstand.

SUMMARY

In accordance with at least some embodiments disclosed herein is the realization that components used with neutral fluid displacement, such as a luer and a post, can break when overlapping and coming into contact with each other, which can result in medical fluid leakage and reduced medical delivery to a patient. When a broken component is located in a connector body, it may not be readily present to a medical professional that the component is broken, leading to delayed response times.

Aspects of the present disclosure provide a needle-free fluid connector assembly that provides a neutral fluid displacement connection while minimizing the risk of breaking one or more components of the needle-free fluid connector assembly. The neutral fluid displacement limits or prevents fluid from entering a catheter lumen during connection or disconnection of a medical fluid.

Accordingly, aspects of the present disclosure provide a fluid connector assembly, comprising: a first member, comprising: a first end comprising a first opening receiving a medical fluid; a second end opposite the first end comprising a second opening; and an internal volume fluidly connecting the first opening and the second opening; and a septum disposed within the second opening preventing the medical fluid from passing therethrough; a second member, comprising: a first end comprising a post; a second end opposite the first end comprising an outlet; at least one aperture extending through the post proximate a proximal end thereof; and a sleeve covering the aperture in a covered configuration and exposing the aperture in an uncovered configuration, wherein the septum receives the post in a coupled configuration, and wherein the septum moves the sleeve from the covered configuration to the uncovered configuration in the coupled configuration thereby fluidly connecting the first opening and the outlet.

Some instances of the present disclosure provide a method for regulating delivery of a medical fluid, the method comprising, by a fluid connector assembly: providing a first member, the first member comprising an internal volume fluidly connecting a proximal end and a distal end thereof; receiving, at an opening at the proximal end of the first member, the medical fluid; receiving, at the distal end of the first member, a septum preventing the medical fluid from passing therethrough; receiving, at the septum, a second member, the second member comprising a post and an aperture extending through the post; receiving, at the post, a sleeve covering the aperture in a covered configuration and exposing the aperture in an uncovered configuration; and forming, based on a displacement of the sleeve into the uncovered configuration by the septum, a fluid pathway that causes the medical fluid that enters the proximal end of the first member to pass through the aperture in a coupled configuration.

Accordingly, the present application addresses several operational challenges encountered in prior neutral displacement connector assemblies that are susceptible to breaking or dislodging from the patient.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIG. 5 illustrates a flowchart showing a method for regulating an intravenous fluid, in accordance with aspects of the present disclosure.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of an IV set, such embodiments can be used in other fluid conveyance systems. Furthermore, various applications of such embodiments and modifications thereto, which may occur to those who are skilled in the art, are also encompassed by the general concepts described herein.

In accordance with some embodiments, the present disclosure includes various features and advantages of maintaining separation between a post and luer, thus minimizing the likelihood of damaging the post and/or the luer.

Figure 1:
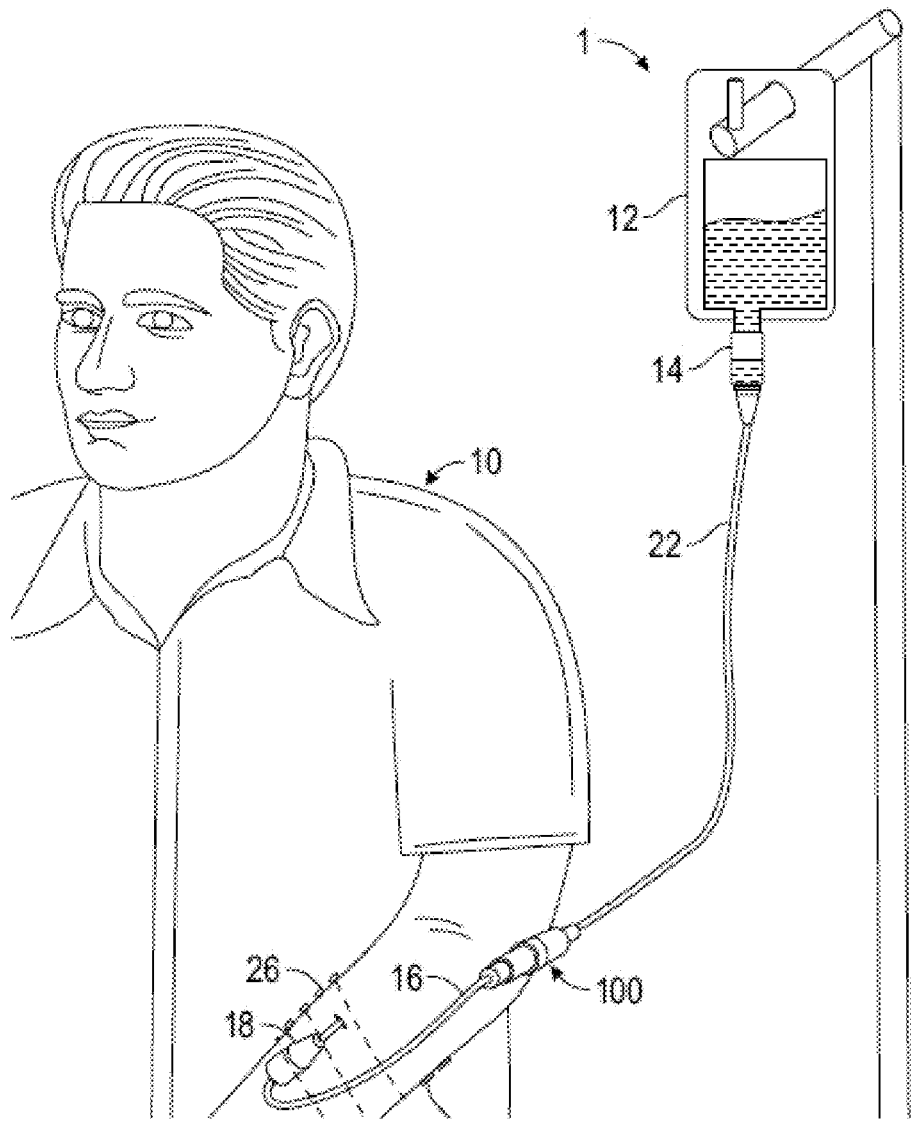
FIG. 1 illustrates an IV set coupled to a patient, in accordance with aspects of the present disclosure.

Referring now to the figures, FIG. 1 illustrates an IV set 1 coupled to a patient 10, in accordance with aspects of the present disclosure. The IV set 1 includes a medical fluid bag 12, a drip chamber 14, and tubing 22. The tubing 22 extends between the drip chamber 14 and a fluid connector assembly 100 of the IV set 1. To resist unintended dislodgement or disconnection of the tubing 16 or the catheter 18 from the patient, tape 26 is placed over the tubing 16 and the catheter 18, so that the tape 26 engages the tubing 16, the catheter 18, and the patient 10.

Figure 2:
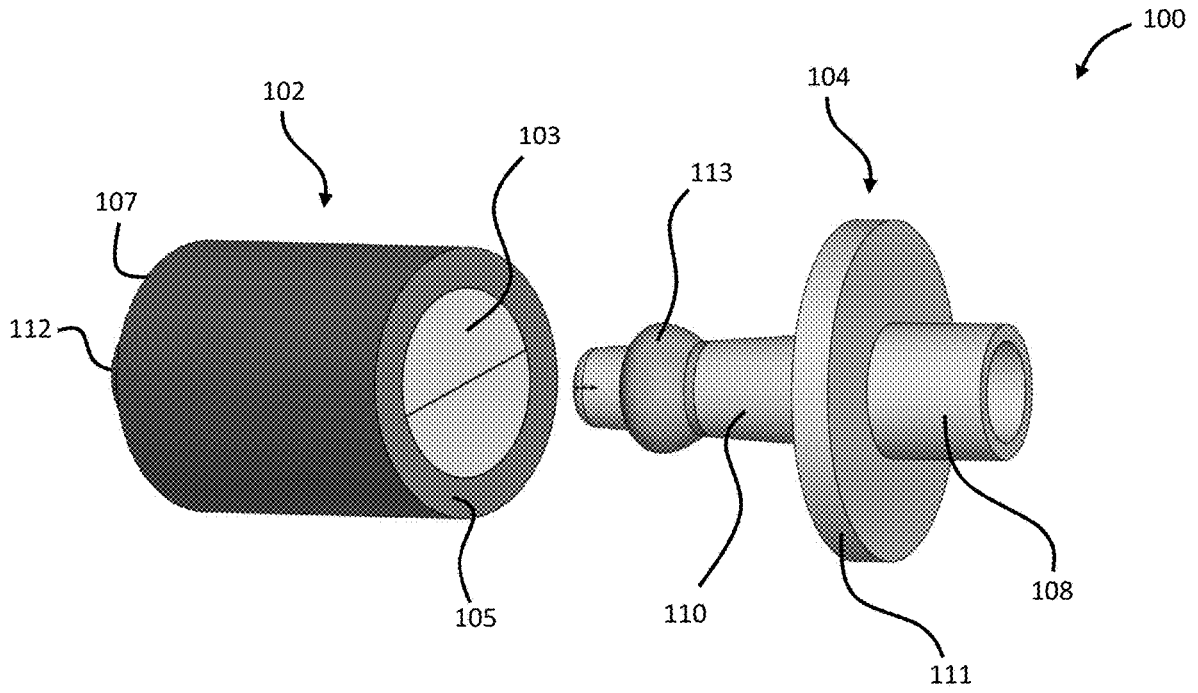
FIG. 2 illustrates an exploded view of a fluid connector assembly for in use with an IV set, in accordance with aspects of the present disclosure.

FIG. 2 illustrates exploded view of the fluid connector assembly 100 for use with an IV set, in accordance with aspects of the present disclosure. The fluid connector assembly 100 is designed for use in medical applications, such as the IV set 1 (shown in FIG. 1) as well as other IV medical fluid delivery applications using catheters, including peripheral intravenous catheters (PIVC), as non-limiting examples.

The fluid connector assembly 100 provides a regulated fluid path throughout the components of the fluid connector assembly 100. As shown, the fluid connector assembly 100 includes a first member 102 used as a central body to carry and/or connect with one or more components. The first member 102 may include a cylindrical, or generally cylindrical, body. Additionally, the first member 102 may include a hollow, or generally hollow, body that forms an internal volume to receive one or more components. The first member 102 may include a septum 103 at a distal end thereof. The septum 103 may include a slit extending across a width of the septum 103. In some embodiments, the slit may extend partially across the width of the septum 103. The septum 103 may be a generally cylindrical shape, but may be shaped to fit within an opening in the end 105 of the first member 102. The first member 102 may include a protrusion 109 extending into the internal volume 124. The protrusion 109 may engage the septum 103 to couple the septum 103 to a distal end of the first member 102.

The fluid connector assembly 100 further includes second member 104 which can couple with the first member 102. As shown, the first member 102 includes an end 105 and an end 107, and the second member 104 can couple to the end 105. The end 105 and the end 107 may be referred to as a first end and a second end, respectively. However, "first" and "second" may be interchangeable for the ends 105 and 107. Also, the second member 104 may be referred to as a connector or medical connector.

In some embodiments, the first member 102 is connected to a medical fluid, such as the medical fluid bag 12 (shown in FIG. 1). Further, in some embodiments, the second member 104 is connected to a catheter line (e.g., tubing 16 in FIG. 1) that delivers the medical fluid to a catheter, such as the catheter 18 (shown in FIG. 1). Also, the second member 104 may take the form of a luer designed to prevent fluid leakage through its connection with the first member 102. In this regard, the second member 104 may conform to standards established by the International Organization for Standards ("ISO") to improve patient safety, minimize medical fluid leakage, and reduce misconnection with other connection devices.

The second member 104 includes an outlet 108 that includes a channel fluidly connected to an opening 116 at the end of the outlet 108. As a result, the outlet 108 acts as a fluid transmission location for the fluid connector assembly 100. Also, the first member 102 includes an inlet 112 that includes an opening (not shown in FIG. 2). The opening of the inlet 112 acts as a fluid inlet of the fluid connector assembly 100. Accordingly, the opening acts as a fluid receiving location for the fluid connector assembly 100. Each of the outlet 108 and inlet 112 can pass centrally, or at least approximately centrally, through an end of the first member 102 and the second member 104, respectively. However, "first" and "second" may be used interchangeably. Also, each of the outlet 108 and inlet 112 includes a cylindrical, or generally cylindrical, shape. However, other shapes are possible.

The second member 104 includes an opening 116 (shown in FIG. 3) formed in a post 110 of the second member 104. The post 110 may be a generally conical shape. In some embodiments, the post 110 is a cannula. However, other shapes are possible. The post 110 may be separated from the outlet 108 by a collar 111. The collar 111 may extent circumferentially from the junction of the post 110 and the outlet 108. The collar may be a generally cylindrical shape with a proximal having a smaller diameter than a distal end thereof. However, other shapes are possible. In some embodiments, the collar 111 is configured to contact the end 105 of the first member 102 when the first member 102 and the second member 104 are coupled in a coupled configuration. In some embodiments the collar 111 is at a generally middle point of a longitudinal axis of the second member 104. In some embodiments, the collar 111 is located on a point of the longitudinal axis closer to a proximal or distal end of the second member 104. In some embodiments, the collar 111 aligns an opening 116 of the post 110 within an internal volume 124 of the first member 102 in the coupled configuration. The opening 116 represents a fluid inlet for the second member 104. The opening 116 is fluidly connected to the outlet 108.

Additionally, the second member 104 includes a sleeve 113. The sleeve 113 may cover the opening 116 to prevent a fluid from entering the second member 104. The sleeve 113 may extend around the post 110, or in some embodiments may only cover the opening 116. The sleeve 113 may be made of silicone or another suitable rubber, plastic or other material. The sleeve 113 may be secured to the post 110 on a distal end thereof, whereas a proximal end thereof is free to slide relative to the post 110. Accordingly, the sleeve 113 is moveable and can compress or fold by an external force (or by multiple external forces) and subsequently return to its original, uncompressed state when an opposite external force is applied. The sleeve 113 is designed to regulate fluid flow through the second member 104. Accordingly, the sleeve 113 acts as a valve for the fluid connector assembly 100. This will be shown in detail below.

Figure 3:
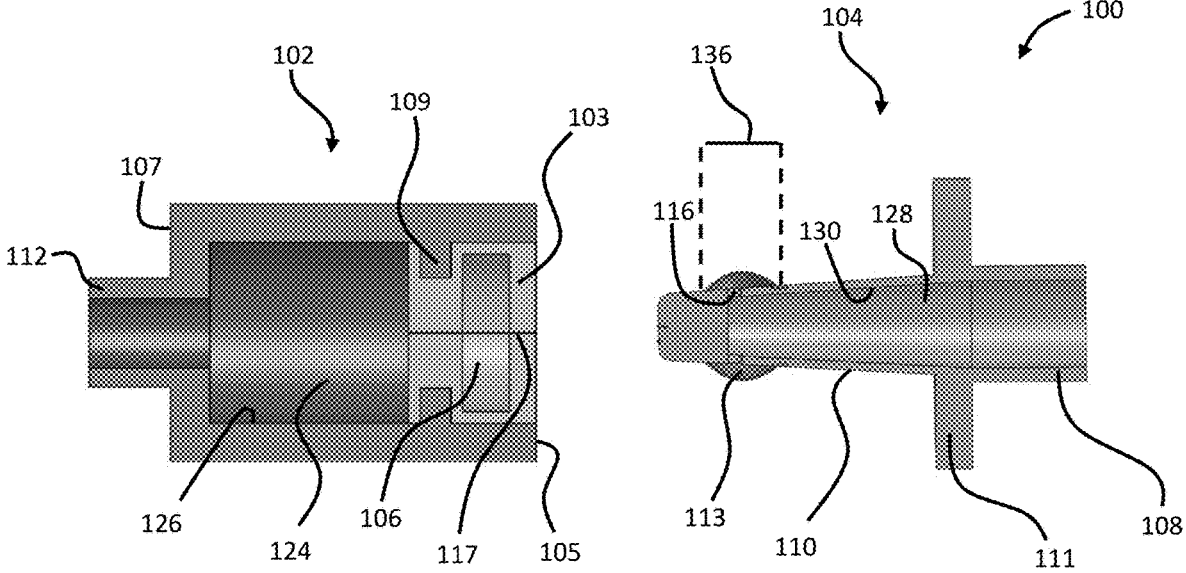
FIG. 3 illustrates a partial cross-sectional view of the fluid connector assembly, showing the first member and the second member, in accordance with aspects of the present disclosure.

FIG. 3 illustrates a partial cross-sectional view of the fluid connector assembly 100, showing the first member 102 and the second member 104, in accordance with aspects of the present disclosure. Based on the hollow design, the first member 102 includes an internal volume 124 that forms a three-dimensional space or void in the first member 102, thus allowing the first member 102 to receive one or more components. For example, the post 110 of the second member 104 can be positioned in the internal volume 124 when the fluid connector assembly 100 is in a coupled configuration. The first member 102 further includes an inner surface 126, or wall, that at least partially defines the internal volume 124 of the first member 102.

Additionally, the post 110 includes an internal volume 128 through which the portion of the outlet 108 lies. The post 110 further includes an inner surface 130, or wall, that at least partially defines the internal volume 128 of the post 110. Also, as shown in FIG. 3, the inner surface 130 of the post 110 meets the outlet 108 at the collar 111. The sleeve 113 prevents fluid flow through the opening 116.

The septum 103 includes a slit 117, or opening, that separates based on an applied force. As shown in FIG. 3, the slit 117 is closed and may resist fluid flow therethrough. However, when the second member 104 is coupled with the first member 102, the post 110 of the second member 104 can engage the septum 103, causing the slit 117 to open based upon the applied force provided by the post 110. In some embodiments, the septum forms a seal between the post 110 and the first member 102 to prevent fluid leakage between the post 110 and the first member 102.

Further, the sleeve 113 includes a dimension 136 that defines a lengthwise dimension of a major axis of the sleeve 113. When no external force is acting on the sleeve 113 to displace (e.g., compress) the sleeve 113, the lengthwise dimension of the sleeve 113 is defined by the dimension 136. Accordingly, the dimension 136 of the sleeve 113 represents an initial dimension, and the size and shape of the sleeve 113 shown in FIG. 3 represents an initial size and shape.

Figure 4:
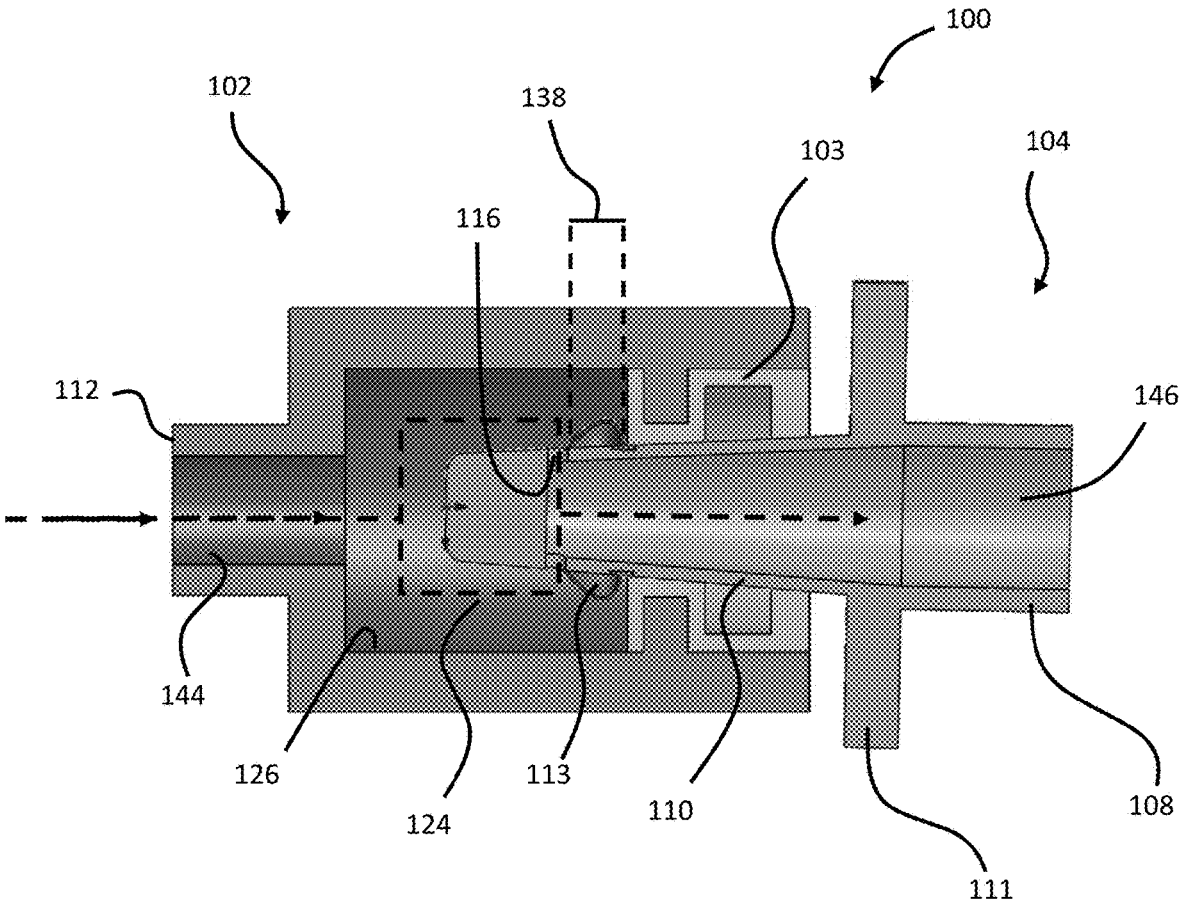
FIG. 4 illustrates a partial cross-sectional view of the fluid connector assembly, showing the second member inserted into the first member, in accordance with aspects of the present disclosure.

FIG. 4 illustrates a partial cross-sectional view of the fluid connector assembly 100, showing the second member 104 inserted into the first member 102, in accordance with aspects of the present disclosure. As shown, the post 110 of the second member 104 is at least partially disposed in the first member 102 and engages the septum 103, causing the slit 117 of the septum 103 to open. Further, the septum 103 engages the sleeve 113, causing the proximal end of the sleeve 113 to translate toward the distal end of the sleeve 113. In some embodiments, the protrusion 109 received within the septum 103 provides the septum 103 with the integrity necessary to translate the sleeve 113 when the post 110 is disposed in the first member 102. In some embodiments, the sleeve 113 folds at a point between the proximal end and the distal end thereof. In some embodiments, the sleeve 113 rolls upon itself in response to engaging the septum 103. In some embodiments, the septum 103 includes a cavity 106 between the proximal end and distal end of the longitudinal axis thereof. In some embodiments, the cavity 106 may be located between the portion configured to receive the protrusion 109 and the portion at the end 105 of the first member 102. The cavity 106 may allow the sleeve 113 to translate radially unopposed when the septum 103 engages the sleeve 113.

For example, the sleeve 113 compresses and reduces to a dimension 138 that is less than the dimension 136 (the original, uncompressed dimension shown in FIG. 3). Further, the displacement of the sleeve 113 causes the opening 116 of the post 110 to open. As a result, fluid passing through the internal volume 124 can further pass through the opening 116 of the post 110. Accordingly, in the uncovered configuration of the sleeve 113, the outlet 108 is fluidly connected to the inlet 112. When the sleeve 113 is reduced to dimension 138, a proximal end thereof can engage the septum to prevent the second member 104 from the first member 102. In some embodiments, the sleeve 113 can prevent separation of the second member 104 from the first member 102 up to a force of 8 pounds. In some embodiments, the force may be between 3 pounds and 8 pounds. In some embodiments, the force may be between 3 pounds and 5 pounds, and in some embodiments, the force may be about 4 pounds. In some embodiments, the force may be less than or about 3 pounds or more than or about 5 pounds. This separation may prevent the fluid connector assembly 100 from unintended dislodgement or disconnection of the tubing 16 or the catheter 18 from the patient.

The arrows with dotted lines show a fluid path through the fluid connector assembly 100. When a medical fluid line is connected to the first member 102, the fluid enters the inlet 112 (i.e., fluid inlet) of the first member 102. The fluid can then pass through the channel 144 of the inlet 112 and enter the internal volume 124 of the first member 102. The fluid can then enter the opening 116 of the post 110 into the internal volume 128, and subsequently pass through a channel 146 of the outlet 108. The fluid can exit the fluid connector assembly 100 through the outlet 108.

Based on the fluid flow through the fluid connector assembly 100, the fluid connector assembly 100 provides neutral fluid displacement in which blood and/or other fluids is/are prevented, or at least substantially limited, from entering a catheter lumen (not shown) positioned in the second member 104 and fluidly connected to the fluid connector assembly 100 during a connector or disconnection between the fluid connector assembly 100 and the catheter lumen, or when the medical fluid line is connected to or disconnected from the first member 102. Based on the features and functionality, the fluid connector assembly 100, unlike positive fluid displacement connector assemblies, does not force fluid into the catheter lumen during a connection or disconnection event. Also, the fluid connector assembly 100, unlike negative fluid displacement connector assemblies, does not allow fluid back into the catheter lumen during a connection or disconnection event. Accordingly, the fluid connector assembly 100 includes a neutral displacement connector assembly.

When the second member 104 is removed from the first member 102, in accordance with aspects of the present disclosure, the septum 103 engages the proximal end of the sleeve 113, moving it away from the distal end of the sleeve 113 and returning the sleeve 113 to its original shape and size. In this regard, the sleeve 113 returns to having the dimension 136, representing the original lengthwise dimension of the sleeve 113 prior to displacement by the septum 103. Further, the slit 117 of the septum 103 closes after removal of the post 110, and the slit 117 prevents fluid passage therethrough. Additionally, the sleeve 113 covers the opening 116 of the post 110 to again seal the opening 116.

FIG. 5 illustrates a flowchart 300 showing a method for regulating delivery of a medical fluid, in accordance with aspects of the present disclosure. Fluid connector assemblies shown or described herein are capable of carrying out the steps of the method shown in the flowchart 300. In this regard, fluid connector assemblies with neutral fluid displacement may carry the steps of the method shown in the flowchart 300.

In step 302, a first member is provided. The first member may act as a central body for the fluid connector assembly. The housing may have a proximal end and a distal end and include an internal volume designed to receive, or at least partially receive, one or more components of the fluid connector assembly.

In step 304, a medical fluid is received at an opening at the proximal end of the first member.

In step 306, a septum is received at an opening at the distal end of the first member. The septum may include a slit extending therethrough. The septum may prevent the medical fluid from passing therethrough.

In step 308, a second member is received at the septum. Further, the second member is received in the internal volume of the first member through the septum. The second member includes a post extending proximally therefrom, which opens the slit in the septum. The post includes an aperture proximate the proximal end thereof extending therethrough.

In step 310, a sleeve is received at the post. Further, the sleeve is configured to cover the aperture in a covered configuration and expose the aperture in an uncovered configuration. Further, a distal end of the sleeve is coupled to the post and a proximal end of the sleeve is movable relative to the post which causes a dimension (e.g., length) of the sleeve to reduce in response to a force acting upon it. However, based on the elastic features of the sleeve, the sleeve may return to its original size and shape when an opposite force acts upon it.

In step 312, a seal is formed based on the displacing of the sleeve into the uncovered configuration. The seal creates a fluid pathway that causes the medical fluid to pass through the aperture of the post of the second connector. Further, the seal promotes neutral fluid displacement by limiting or preventing blood and/or other fluid from entering a catheter lumen when a connection or disconnection with the fluid connection assembly occurs.

The features of the present disclosure provide a fluid connector assembly with a sleeve that can be displaced to form a fluid pathway therebetween. When a first and a second member are coupled together, the sleeve can displace and allow fluid flow. However, if the member that displaces the sleeve is separated from the second member, whether unintentionally or intentionally, the fluid pathway the fluid connector assembly closes or is obstructed to prevent fluid loss therefrom, as the sleeve returns to its uncompressed state and closes off the fluid pathway. The features of the present disclosure also provide that upon separation of the first and second members, any of the first and second members can be cleaned and disinfected, and the first and second members can be once again coupled together to cause the sleeve to form a fluid pathway therebetween.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, clause 8 or clause 15. The other clauses can be presented in a similar manner.

Clause 1. A fluid connector assembly, comprising: a first member, comprising: a first end comprising a first opening receiving a medical fluid; a second end opposite the first end comprising a second opening; and an internal volume fluidly connecting the first opening and the second opening; and a septum disposed within the second opening preventing the medical fluid from passing therethrough; a second member, comprising: a first end comprising a post; a second end opposite the first end comprising an outlet; at least one aperture extending through the post proximate a proximal end thereof; and a sleeve covering the aperture in a covered configuration and exposing the aperture in an uncovered configuration, wherein the septum receives the post in a coupled configuration, and wherein the septum moves the sleeve from the covered configuration to the uncovered configuration in the coupled configuration thereby fluidly connecting the first opening and the outlet.

Clause 2. The fluid connector assembly of Clause 1, wherein a proximal end of the sleeve is folded toward a distal end of the sleeve in the uncovered configuration.

Clause 3. The fluid connector assembly of Clause 2, wherein the sleeve engages a proximal end of the septum to resist separation of the first member and the second member in the uncovered configuration.

Clause 4. The fluid connector assembly of Clause 3, wherein the sleeve is resists separation of the first member and the second member up to a force of between 3 pounds and 5 pounds.

Clause 5. The fluid connector assembly of Clause 1, wherein the second member further comprises a collar at a base of the post to align the aperture with the internal volume in the coupled configuration.

Clause 6. The fluid connector assembly of Clause 5, wherein the second end of the first member is a generally flat surface engaging the collar of the second member in the coupled configuration.

Clause 7. The fluid connection assembly of Clause 1, wherein the sleeve is configured to cover the aperture upon separation of the first member and the second member.

Clause 8. The fluid connector assembly of Clause 1, wherein the septum includes a slit extending at least partially across a width of the septum.

The fluid connector assembly of Clause 1, wherein the sleeve extends circumferentially around the post.

Clause 10. The fluid connector assembly of Clause 1, wherein the sleeve covers only a portion of the post defining the aperture.

Clause 11. The fluid connector assembly of Clause 1, wherein the post is a generally conical shape.

Clause 12. The fluid connector assembly of Clause 1, wherein the first member is a generally cylindrical side.

Clause 13. The fluid connection assembly of Clause 1, wherein the post is a post.

Clause 14. The fluid connection assembly of Clause 1, wherein the internal volume comprises a protrusion configured to couple the septum to an internal surface of the first member.

Clause 15. A method for regulating delivery of a medical fluid, the method comprising, by a fluid connector assembly: providing a first member, the first member comprising an internal volume fluidly connecting a proximal end and a distal end thereof; receiving, at an opening at the proximal end of the first member, the medical fluid; receiving, at the distal end of the first member, a septum preventing the medical fluid from passing therethrough; receiving, at the septum, a second member, the second member comprising a post and an aperture extending through the post; receiving, at the post, a sleeve covering the aperture in a covered configuration and exposing the aperture in an uncovered configuration; and forming, based on a displacement of the sleeve into the uncovered configuration by the septum, a fluid pathway that causes the medical fluid that enters the proximal end of the first member to pass through the aperture in a coupled configuration.

Clause 16. The method of Clause 15, wherein: the septum comprises a slit; and receiving the second member comprises the post extending through the slit of the septum.

Clause 17. The method of claim 16, wherein receiving the second member comprises folding a proximal end of the sleeve toward a distal end thereof.

Clause 18. The method of Clause 17, wherein maintaining the coupled configuration comprises the sleeve engaging a proximal end of the septum to resist separation of the first member and the second member.

Clause 19. The method of Clause 15, wherein: the distal end of the first member comprises a generally flat surface; the second member comprises a collar at a distal end of the post; and receiving the second member is prevented when the collar engages the distal end of the first member.

Clause 20. The method of Clause 15, wherein separating the first member and the second member comprises the sleeve returning to the covered configuration and the septum preventing the medical fluid from passing therethrough.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A fluid connector assembly, comprising:
a first member, comprising:
    a first end comprising a first opening receiving a medical fluid;
    a second end opposite the first end comprising a second opening; and
    an internal volume fluidly connecting the first opening and the second opening; and
    a septum disposed within the second opening preventing the medical fluid from passing therethrough;
a second member, comprising:
    a first end comprising a post;
    a second end opposite the first end comprising an outlet;
    at least one aperture extending through the post; and
    a sleeve moveable relative to the post covering the aperture in a covered configuration and exposing the aperture in an uncovered configuration,
wherein the septum receives the post in a coupled configuration, and
wherein the septum moves the sleeve from the covered configuration to the uncovered configuration in the coupled configuration thereby fluidly connecting the first opening and the outlet, and the sleeve engages a proximal end of the septum to resist separation of the first member and the second member in the uncovered configuration.

2. The fluid connector assembly of claim 1, wherein a proximal end of the sleeve is displaced toward a distal end of the sleeve in the uncovered configuration.

3. The fluid connector assembly of claim 1, wherein the sleeve in the uncovered configuration resists separation of the first member and the second member up to a force of between 3 pounds and 5 pounds.

4. The fluid connector assembly of claim 1, wherein the second member further comprises a collar at a base of the post aligning the aperture with the internal volume in the coupled configuration.

5. The fluid connector assembly of claim 4, wherein the second end of the first member is a generally flat surface engaging the collar of the second member in the coupled configuration.

6. The fluid connection assembly of claim 1, wherein the sleeve is configured to cover the aperture upon separation of the first member and the second member.

7. The fluid connector assembly of claim 1, wherein the septum includes a slit extending at least partially across a width of the septum.

8. The fluid connector assembly of claim 1, wherein the sleeve extends circumferentially around the post.

9. The fluid connector assembly of claim 1, wherein the sleeve covers only a portion of the post defining the aperture.

10. The fluid connector assembly of claim 1, wherein the post is a generally conical shape.

11. The fluid connector assembly of claim 1, wherein the first member has a generally cylindrical shape.

12. The fluid connection assembly of claim 1, wherein the post is a cannula.

13. The fluid connection assembly of claim 1, wherein the internal volume comprises a protrusion configured to couple the septum to an internal surface of the first member.

14. A method for regulating delivery of a medical fluid, the method comprising, by a fluid connector assembly:
    providing a first member, the first member comprising an internal volume fluidly connecting a proximal end and a distal end thereof;
    receiving, at an opening at the proximal end of the first member, the medical fluid;
    receiving, at the distal end of the first member, a septum preventing the medical fluid from passing therethrough;
    receiving, at the septum, a second member, the second member comprising a post and an aperture extending through the post;
    receiving, at the post, a sleeve covering the aperture in a covered configuration and exposing the aperture in an uncovered configuration; and
    forming, based on a displacement of the sleeve into the uncovered configuration by the septum, a fluid pathway that causes the medical fluid that enters the proximal end of the first member to pass through the aperture in a coupled configuration, wherein engagement of the sleeve against a proximal end of the septum resists separation of the first member and the second member in the coupled configuration.

15. The method of claim 14, wherein:
    the septum comprises a slit; and
    receiving the second member comprises the post extending through the slit of the septum.

16. The method of claim 15, wherein receiving the second member comprises folding a proximal end of the sleeve toward a distal end thereof.

17. The method of claim 14, wherein:
    the distal end of the first member comprises a generally flat surface;
    the second member comprises a collar at a distal end of the post; and
    receiving the second member is prevented when the collar engages the distal end of the first member.

18. The method of claim 14, wherein separating the first member and the second member comprises the sleeve returning to the covered configuration and the septum preventing the medical fluid from passing therethrough.

* * * * *